United States Patent
Asselin et al.

[11] Patent Number: 5,990,307
[45] Date of Patent: Nov. 23, 1999

[54] PROCESS FOR THE PREPARATION OF [2-((8.9)-DIOXO-2,6-DIAZABICYCLO [5.2.0]-NON-1(7)-EN-2YL) ETHYL]PHOSPHONIC ACID

[75] Inventors: Andre A. Asselin, Mahwah, N.J.; William A. Kinney, Richboro, Pa.; Jean Schmid, Chester, N.Y.

[73] Assignee: American Home Products Corporation, Madison, N.J.

[21] Appl. No.: 09/127,202

[22] Filed: Jul. 31, 1998

Related U.S. Application Data

[60] Provisional application No. 60/054,553, Aug. 1, 1997.

[51] Int. Cl.⁶ .......................... C07D 223/32; C07C 69/00
[52] U.S. Cl. ............................ 540/542; 560/129
[58] Field of Search .................... 540/542; 560/129

[56] References Cited

U.S. PATENT DOCUMENTS 5,168,103  12/1992  Kinney et al. .................... 514/221

FOREIGN PATENT DOCUMENTS 0496561  7/1992  European Pat. Off. .
1518660  7/1965  Germany .

*Primary Examiner*—Mukund J. Shah
*Assistant Examiner*—Bruck Kifle
*Attorney, Agent, or Firm*—Steven R. Eck; Arthur G. Seifert

[57] ABSTRACT

This invention relates to a process for the preparation of the formula I compound [2-((8,9)-dioxo-2,6-diazabicyclo [5.2.0]-non-1(7)-en-2-yl)ethyl]phosphonic acid, a NMDA antagonist useful as an anticonvulsant and neuroprotectant in situations involving excess release of excitatory amino acids.

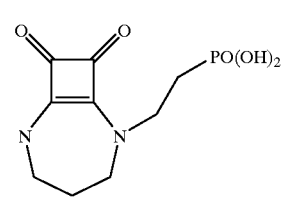

In the process of the present invention, 3-aminopropyl carbamic acid 1,1-dimethylethyl ester is reacted with a dialkyl vinylphosphonate to obtain N-[3-(t-butyloxycarbonyl-amino)propyl]-2-aminoethylphosphonic acid dialkyl ester (d) in 80% yield. Reaction of (d) with a 3,4-dialkoxy-cyclobut-3-en-1,2-dione gives [3-[[2-(dialkoxyphosphoryl-)ethyl]-(2-alkoxy-3,4-dioxo-1,2-cyclobuten-1-yl)amino] propyl] carbamic acid 1,1-dimethylethyl ester (e) in 96% yield. Deprotection and cyclization of (e) in trifluoroacetic acid gives [2-((8,9)-dioxo-2,6-diazabicyclo[5.2.0]-non-1(7)-en-2-yl)ethyl]phosphonic acid dialkyl ester (c) in 58% yield. The phosphonic acid diethyl ester (c) was treated with bromotrimethylsilane to give compound I.

15 Claims, No Drawings

PROCESS FOR THE PREPARATION OF [2-((8.9)-DIOXO-2,6-DIAZABICYCLO [5.2.0]-NON-1(7)-EN-2YL) ETHYL]PHOSPHONIC ACID

This application claims the benefit of U.S. Provisional Application Ser. No. 0/054,553, filed Aug. 1, 1997.

This invention relates to a process for the preparation of the formula I compound [2-((8,9)-dioxo-2,6-diazabicyclo[5.2.0]-non-1(7)-en-2-yl)ethyl]phosphonic acid, a NMDA antagonist useful as an anticonvulsant and neuroprotectant in situations involving excess release of excitatory amino acids.

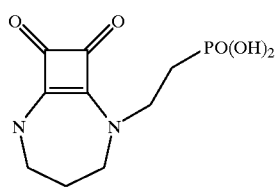

The formula I compound and a process for its preparation are disclosed in U.S. Pat. No. 5,168,103. In the disclosed process, 3-aminopropyl carbamic acid phenylmethyl ester is reacted with 2-oxoethylphosphoric acid dialkyl ester and sodium cyanoborohydride to obtain the intermediate[3-[[2-(dialkoxyphosphinyl)ethyl]amino]propyl]carbamic acid phenylmethyl ester (a) in 36% yield. Reaction of (a) with a 3,4-dialkoxy (or 3,4-diarylalkoxy)-cyclobut-3-en-1,2-dione such as 3,4-diethoxycyclobut-3-en-1,2-dione yields 3-[[2-(dialkoxyphosphoryl)ethyl]-(2-alkoxy-3,4-dioxo-1-cyclobuten-1-yl)amino]propyl-carbamic acid phenylmethyl ester (b) in 89% yield. Removal of the benzyloxycarbonyl protecting group and cyclization of (b) to [2-((8,9)-dioxo-2,6-diazabicyclo[5.2.0]-non-1(7)-en-2-yl)ethyl]phosphonic acid dialkyl ester (c) is accomplished in 62% yield by treating (b) with 10% palladium on carbon and 1,4-cyclohexadiene. Treatment of the bicyclic diester (c) with bromotrimethylsilane affords [2-((8,9)-dioxo-2,6-diazabicyclo-[5.2.0]-non-1(7)-en-2-yl)ethyl]phosphonic acid (I) in 78% yield. The overall yield for the sequence of reactions is 15.5%.

In the processes of the present invention, as illustrated in Step II of Scheme I below, a 3-aminopropyl carbamic acid dialkyl ester (IV) is, instead, reacted with a dialkyl vinylphosphonate (V) to obtain the N-[3-(t-butyloxy-carbonylamino)propyl]-2-aminoethylphosphonic acid dialkyl ester (VI). Further improvements provided by the present invention over the process of U.S. Pat. No. 5,168,103 as noted below, increase the overall yield to produce I to 38.8%.

One aspect of this invention is a process for the preparation of [2-((8,9)-dioxo-2,6-diazabicyclo[5.2.0]non-1 (7)-en-2-yl)ethyl]phosphonic acid which comprises the following steps:

a) reacting a 3,4-di-$C_1$-$C_4$alkoxycyclobut-3-en-1,2-dione with a di-$C_1$-$C_6$alkyl ester of N-[3-(t-butyloxycarbonylamino)propyl]-2-aminoethylphosphonic acid to give 3-[[2-(di-$C_1$-$C_6$alkoxyphosphoryl)ethyl]-(2-$C_1$-$C_6$alkoxy-3,4-dioxo-1-cyclobuten-1-yl)amino]propyl-carbamic acid tert-butyl ester;

b) deprotecting the 3-amino group of the product of step (a);

c) cyclizing the product of step (b) to form the bicyclic intermediate [2-((8,9)-dioxo-2,6-diazabicyclo[5.2.0]non-1(7)-en-2-yl)ethyl]phosphonic acid di-$C_1$-$C_6$alkyl ester; and d) converting the di-$C_1$-$C_6$alkyl ester of step (c) to the phosphonic acid product.

Step (a) is preferably carried out in anhydrous methanol or ethanol at ambient temperatures (25–30° C.). Steps (a), (b) and (c) are preferably run in situ. Step (b) is preferably carried out in methylene chloride at −5° C. to 25° C. Step (d) is preferably carried out in methylene chloride or acetonitrile at about 20° C. The preferred 3,4-di-$C_1$-$C_4$ alkoxycyclobut-3-en-1,2-dione in step (a) is 3,4-diethoxycyclobut-3-en-1,2-dione.

In another aspect of the invention, the di-$C_1$-$C_6$ alkyl ester of N-[3-(t-butyloxy-carbonylamino)propyl]-2-aminoethylphosphonic acid of step (a) is prepared by a process which comprises reacting a vinylphosphonate di-$C_1$-$C_6$ alkyl ester with 3-aminopropyl carbamic acid 1,1-dimethylethyl ester. The preferred vinylphosphonate di-$C_1$-$C_6$ alkyl ester is dimethyl vinylphosphonate or is diethyl vinylphosphonate, of which dimethyl vinylphosphonate is most preferred.

In another aspect, the invention provides the following compounds:

a compound which is an N-[3-(t-butyloxycarbonylamino)propyl]-2-aminoethylphosphonic acid di-$C_1$-$C_6$ alkyl ester;

a compound which is N-[3-(t-butyloxycarbonylamino)propyl]-2-aminoethylphosphonic acid dimethyl ester or N-[3-(t-butyloxycarbonylamino)propyl]-2-aminomethylphosphonic acid diethyl ester;

a compound which is a 3-[[2-(di -$C_1$-$C_6$ alkoxy-phosphoryl)ethyl]-(2-$C_1$-$C_4$ alkoxy-3,4-dioxocyclobut-1-enyl)amino]propylcarbamic acid tert-butyl ester; and a compound which is 3-[[2-(diethoxy-phosphoryl)ethyl]-(2-ethoxy-3,4-dioxocyclobut-1-enyl)amino] propylcarbamic acid tert-butyl ester or is 3-[[2-(diethoxy-phosphoryl)ethyl]-(2-methoxy-3,4-dioxocyclobut-1-enyl)arninolpropylcarbamic acid tert-butyl ester.

The process of the present invention is illustrated in Scheme 1 below, where "alkyl" is represented by the ethyl group and "alkoxy" is represented by the ethoxy group, and is further described as follows:

In Step 1, 1,3-diaminopropane (II) is reacted with a di-t-butylcarbonate (III) to give 3-aminopropyl carbamic acid 1,1-dimethylethyl ester (IV).

In Step 2, the carbamic acid ester IV is reacted with a di-$C_1$-$C_6$alkyl vinylphosphonate (V), to give N-[3-(t-butyloxy-carbonylamino)propyl]-2-aminoethylphosphonic acid di-$C_1$-$C_6$alkyl ester (VI). In the illustrated case where V is diethyl vinylphosphphonate, this step provides an 80% yield. However, dimethyl vinylphosphonate provides comparable yields and is preferred commercially because it is more readily available in larger quantities.

In Step 3, aminophosphonic acid di-$C_1$-$C_6$alkyl ester (VI) is reacted with a 3,4-di-$C_1$-$C_4$alkoxycyclobut-3-en-1,2-dione (VII) to give a 3-[[2-(di-$C_1$-$C_6$alkoxyphosphoryl)ethyl]-(2-$C_1$-$C_4$alkoxy-3,4-dioxo-1-cyclobuten-1-yl)amino]propyl-carbamic acid 1,1-dimethylethyl ester (VIII). In the illustrated case where alkyl refers to ethyl in both instances, this step provides a 96% yield. This step is preferably carried out in anhydrous methanol or ethanol at ambient temperatures.

In step 4, deprotection of (VIII) in trifluoro-acetic acid followed by cyclization with 20 triethylamine as a cyclizing agent gives [2-((8,9)-dioxo-2,6-diazabicyclo[5.2.0]-non-1 (7)-en-2-yl)ethyl]-phosphonic acid di-$C_1$-$C_6$alkyl ester (IX). In the illustrated case the yield of the product IX is 58% yield. The deprotection is preferably carried out in methylene chloride at −5° C. to 25° C. The cyclization is preferably carried out in methylene chloride or acetonitrile, with methylene chloride being particularly preferred, at about 20° C.

In Step 5, the phosphonic acid diethyl ester (IX) is treated with bromotrimethylsilane to give compound I in 87% yield.

The process according to this invention is outlined in the following scheme I. In this scheme, "alkyl" is represented by the ethyl group and "alkoxy" is represented by the ethoxy group.

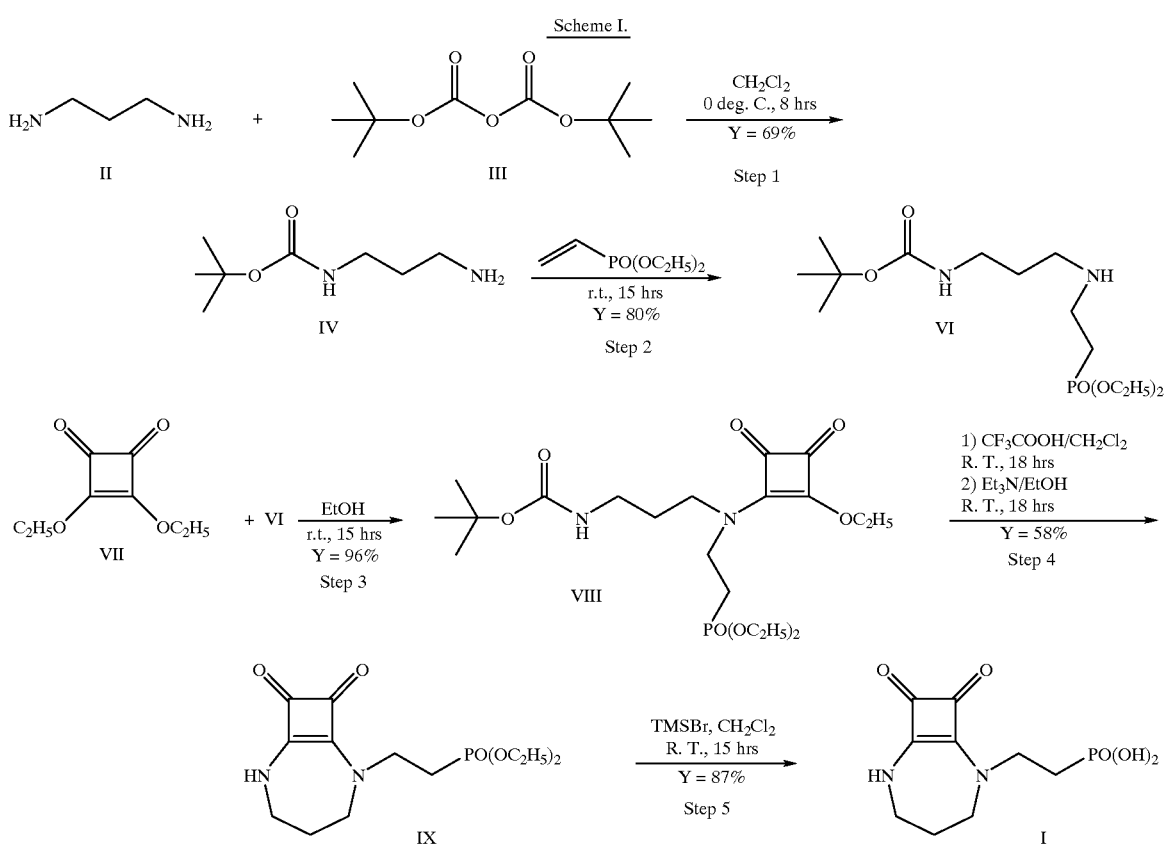

The overall yield for preparing [2-((8,9)-dioxo-2,6-diazabicyclo[5.2.0]-non-1(7)-en-2-yl)ethyl]phosphonic acid (I) according to the process of this invention is 38.8%, a considerable improvement over the 15.5% yield disclosed in U.S. Pat. No. 5,168,103.

Steps 2, 3 and 4 are preferably done in situ.

In the reaction sequence above, the term "alkyl" means a $C_1$–$C_6$ alkyl, straight or branched, and the term "alkoxy" means a $C_1$–$C_6$ alkoxy group, except with respect to the squarate compounds VII where alkyl means methyl, ethyl or butyl. The yields refer to specific instances where "alkyl" is ethyl and "alkoxy" is ethoxy. Advantages of the process of this invention are several fold. First, 1,3-propanediamine is mono-protected in excellent yield with di-t-butyldicarbonate, a reaction that is less hazardous than using benzylchloroformate to prepare a benzyloxycarbamate protecting group. Second, the monoprotected-1,3-propanediamine is reacted with diethyl vinylphosphonate in excellent yield without employing additional reagents such as sodium cyanoborohydride and acid, each of which is not without hazard, which were required when using diethyl 2-oxoethylphosphonate as previously disclosed. Third, the t-butyloxycarbonyl group is removed readily with acid whereas the removal of the benzyloxycarbonyl group required the use of palladium catalyst and a hydrogen source.

The following specific examples are included to illustrate the process of this invention and should not be construed as limiting to the process of this invention in any way. Those skilled in the art may be aware of still other procedures or modifications which may be used in an equivalent manner to perform the invention process.

EXAMPLE 1

3-(t-Butyloxycarbonylamino)propanamine

To a solution of 1,3-diaminopropane (500 g, 6.75 moles; Aldrich D2, 360-2) in tetrahydrofuran (1.6 l) at from −3° C. to +2° C. with stirring was added dropwise a solution of di-t-butyldicarbonate (300 g, 1.375 mole; Aldrich 19, 913-3) in tetrahydrofuran (800 mL) over a period of ~8 hr. The resulting white suspension was stirred at 0° C. and let slowly warm to ambient temperature overnight. The reaction mixture was concentrated in vacuo and the residue was taken up in a mixture of ethyl acetate and saturated sodium chloride solution. The aqueous layer was extracted with ethyl acetate. The combined extracts were washed once with sat. sodium chloride, dried over magnesium sulfate and filtered to yield an oil (~245 g, quantitative). The oil was suspended in water (200 mL) and cooled to 0° C. to −5° C. An aqueous solution of bromo cresol green (3 mL, 0.04% in water; Aldrich 31, 870-1) was added to result in a blue solution. With vigorous stirring (IN hydrochloric acid (1.4 L) was added dropwise to give a light blue to green/yellow colored solution (pH ~5–6, pH-paper). This suspension was extracted with methylene chloride (2×300 mL) and the aqueous layer made basic with 2.5 n sodium hydroxide to pH ~12. The basis aqueous layer was extracted with methylene chloride (5×300 mL) and the organic layer was washed with saturated sodium chloride solution (2×100 mL), dried over anhydrous potassium carbonate powder, filtered through Celite and concentrated to give the title compound as a faint bluish oil which crystallized on standing (165 g, 69%) (very hygroscopic solids).

NMR (CDCl$_3$, 400 MHz): 1.43 (s, 9H), 1.61 (p, 2H), 1.59 (s, 2H), 2.76 (t, 2H), 3.20 (q, 2H), 4.95 (br, 1H).

EXAMPLE 2

N-[3-(t-Butyloxycarbonylamino)propyl]-2-aminoethylphosphonic acid diethyl ester

To a solution of 3-(t-butyloxycarbonylamino) propanamine (77 g, 0.44 mole) in methanol (500 mL) was added diethyl vinylphosphonate 97% (75 g, 0.44 mole; Aldrich 11,613-0) under nitrogen and kept in a water bath at ~20° C. for 48 hr. The reaction mixture was concentrated in vacuo and the residue (~160 g) was put on a pad of "Florisil" (3"×6") and eluted with methylene chloride/hexane 1:1, methylene chloride and finally 10% methanol/methylene chloride to give the title compound as a colorless oil (121 g, 80%).

NMR (CDCl$_3$, 400 MHz): 1.32 (t, 6H), 1.43 (s, 9H), 1.65 (t, 2H), 1.80 (br, 1H), 1.97 (dt, 2H), 2.67 (t, 2H), 2.85 (dt, 2H), 3.20 (q, 2H), 4.09 (m, 4H), 5.08 (br, 1H).

EXAMPLE 3

3-[[2-(Diethoxy-phosphoryl)-ethyl]-(2-ethoxy-3,4-dioxocyclobut-1-enyl)amino]propylcarbamic acid tert-butyl ester To a solution of 3,4-diethoxy-3-cyclobutene-1,2-dione (45 g, 0.265 mole; Aldrich 31,077-8) in absolute ethanol (1.2 L) under nitrogen was added dropwise a solution of N-[3-(t-butyloxycarbonylamino)propyl]-2-aminoethylphosphonic acid diethyl ester (80 g, 0.24 mole) in absolute ethanol (600 mL) and the reaction mixture was stirred at ambient temperature 15 hr. The reaction mixture was concentrated in vacuo and the residue was put on a pad of silica gel (6"×4") and eluted first with a mixture of methylene chloride/hexane 1:1 to remove excessive 3,4-diethoxy-3-cyclobutene-1,2-dione and finally with 10% methanol/methylene chloride to yield the title compound after evaporation as a viscous oil (107 g, 96%).

NMR: (CDCl$_3$, 400 MHz): 1.34 (t, 6H), 1.43 (s, 9H), 1.46 (t, 3H), 1.80 (m, 2H), 2.12 (m, 2H), 3.14 (m, 2H), 3.49 (t, 1H), 3.66 (m, 1H), 3.73 (t, 1H), 3.90 (m, 1H), 4.10 (m, 4H), 4.74 (m, 4H), 5.05 (br, H).

EXAMPLE 4

[2-(8,9-Dioxo-2,6-diazabicyclo[5.2.0]non-1(7)-en-2-yl)ethyl]phosphonic Acid Diethyl Ester A solution of N-[3-(t-butoxycarbonylamino)propyl]-N-[4-ethoxy-2,3-dioxocyclobut-1-ene-1-yl]-2-aminoethylphosphonic acid diethyl ester (100 g, 0.22 mole) in methylene chloride (600 mL) was cooled in ice and treated with trifluoroacetic acid (300 mL). The reaction mixture was left to warm to ambient temperature overnight. The solution was concentrated in vacuo at max. 40° C. and co-evaporated with toluene (2×500 mL) to yield a viscous oil (159.5 g) which was dissolved in absolute ethanol (1.5 L) and added dropwise over eight hours to a solution of triethylamine (350 mL) in ethanol (1.5 L) and stirred for 8 hr. at room temperature. The reaction mixture was concentrated in vacuo to an oil which was taken up in ethyl acetate (1 L). Compound crystallized and was cooled in ice, filtered and washed with ethyl acetate and finally hexane to give the title compound as a white compound (40 g, 58%).

NMR (CDCl$_3$, 400 MHz): 1.34 (t, 6H), 2.06 (m, 2H), 2.20 (dt, 2H), 3.50 (m, 4H), 4.05 (m, 2H), 4.15 (m, 4H), 7.87 (br, 1H). MS (DEI) M+m/z 316. LC analysis (column: Microsorb-MV C18, 150×4.6 mm; Eluent: 30/70 MeOH/ 0.01 M NH$_4$H$_2$PO$_4$ pH 4.7; Flow rate: 1 mL/min; UV detector at 210 nm; Analysis: Calc'd. for C$_{13}$H$_{21}$N$_2$O$_5$P: C, 49.36; H, 6.69; N, 8.85%. Found: C, 49.47; H, 6.74; N, 8.77%.

EXAMPLE 5

[2-(8,9-Dioxo-2,6-diazabicyclo[5.2.0]non-1(7)-en-2-yl)ethyl]-phosphonic Acid

Under N$_2$ bromotrimethylsilane (83 mL, 96.3 g, 0.63 mole; Aldrich 19,440-9) was added dropwise at a fast rate to a solution of [2-(8,9-dioxo-2,6-diazabicyclo[5.2.0]non-1(7)-en-2-yl)ethyl]phosphonic acid diethyl ester (37.6 g, 0.12 mole) in methylene chloride (350 mL). The reaction mixture was kept in a water bath at approximately 20° C. for 15 hr. The clear solution was concentrated in vacuo and the foamy residue was taken up in acetone (600 mL) with vigorous shaking to result in a thin suspension. Water (50 mL, 2.78 moles) was added to give a gummy precipitate which solidified instantly. The suspension was shaken vigorously for 10 minutes, filtered and washed with acetone to give a yellow solid compound. The solids were taken up in boiling water (450 mL) and the hot solution was filtered through a fluted filter paper to remove a small amount of insoluble material. The clear aqueous solution was cooled in ice and crystallization began at once. The thick crystalline mass was diluted by slow addition of acetone (800 mL), kept cold for 1 hr, filtered and washed with acetone and then hexane to give the title compound as a pale yellow solid (20.2 g). A second crop from the mother liquor (100% purity by LC) yielded an additional amount (6.5 g) for a total yield of 87%.

NMR (DMSO-d$_6$, 400 Mhz): 1.90 (m, 4H), 3.25 (m, 2H), 3.36 (m, 2H), 3.84 (q, 2H), 8.45 (s, 1H). LC analysis: (Column: Nova Pak C18, 300×3.9 mm; Eluent: 20/80 MeOH/0.005 M Pic A; Flowrate: 1 mL/min; UV detectors at 210 nm). Analysis: Calc'd. for C$_9$H$_{13}$N$_2$O$_5$P.0.1 H$_2$O: C, 41.26; H, 5.08; N, 10.69%; Found: C, 41.17; H, 5.04; N, 10.42%; Karl-Fischer analysis: 0.55% H$_2$O; MS: –FAB [M–H]$^-$ m/z 259.

EXAMPLE 6

Preparation of 3-(t-Butoxycarbonylamino) propanamine ("t-BOC-Propanamine")

A solution of di-t-butyldicarbonate (0.50 Kg, 2.29 moles) in methanol was added to an excess (5 equivalents) of 1,3-diaminopropane (0.83 Kg, 11.2 moles) over a 4 hour period at 25–30° C. The product 1,3-Diaminopropane t-butoxycarbonate was filtered off and the methanol removed by vacuum distillation. The residual oil was taken into ethyl acetate, washed with brine, water added, and the pH adjusted to 5.5. The layers were separated and the aqueous phase made strongly alkaline. The alkaline aqueous solution was extracted six times with toluene. The combined toluene extracts were dried over sodium sulfate and concentrated to afford t-BOC-propanamine (0.365 Kg) in a 77.4% yield, 11.5% total impurities.

EXAMPLE 7

Preparation of [2-(8,9-Dioxo-2,6-diazabicyclo[5.2.0] non-1(7)-en-2-yl]phosphonic acid, dimethyl ester ("Dimethyl Phosphonate Ester")

A. Formation of t-BOC-phosphonate Dimethyl Ester

A solution of t-BOC-Propanamine, 98% (0.67 Kg, 3.77 moles) and dimethylvinylphosphonate (0.59 Kg, 4.12 moles) in anhydrous methanol (2.7 L) were stirred at room temperature for 2 days to give a solution of the Dimethyl Phosphonate Ester product.

B. Formation of t-BOC-Phosphonate Dimethyl Ethyl Squarate

The Dimethyl Phosphonate Ester product solution in A was then added to a solution of 3,4-diethoxy-3-cyclobutene-1,2-dione ("Ethyl Squarate") (0.55 Kg, 3.23 moles) in anhydrous methanol (3.24 L) over a six hour period. After stirring at 0–5° C. overnight the reaction mixture was concentrated by distillation. Toluene (1 L) added and the distillation repeated to a final volume of 1.6 L 3-[[2-(Diethoxy-phosphoryl)-ethyl]-(2-ethoxy-3,4-dioxocyclobut-1-enyl)amino]propylcarbamic acid tert-butyl ester ("t-BOC-Phosphonate Dimethyl Ethyl Squarate").

C. Formation of Deprotected Phosphonate Dimethyl Ethyl Squarate

To the product solution of t-BOC-Phosphonate Dimethyl Ethyl Squarate from B was added toluene (5.0 L) at 0–5° C., followed by trifluoroacetic acid (4.71 Kg, 41.31 moles) over 0.25–5 hrs. while keeping the temperature under 15° C. After stirring for 4 hours at room temperature, the reaction mixture was concentrated to afford the crude deprotected Phosphonate Dimethyl Ethyl Squarate.

D. Formation of Dimethyl Phosphonate Ester

Anhydrous methanol (4.5 L) was added to the reaction product concentrate from C, and the resulting solution was added over a 6 hour period to a solution of excess triethylamine (2.9 Kg, 28.66 moles) in anhydrous methanol at room temperature. The resulting mixture was concentrated, followed by the addition of ethyl acetate which precipitated out the titled Dimethyl Phosphonate Ester product. After filtration and washing of the cake with cold ethyl acetate a 50.4% yield of [2-(8,9-Dioxo-2,6-diazabicyclo[5.2.0]non-1(7)-en-2-yl)ethyl]phosphonic Acid Diethyl Ester ("Dimethyl Phosphonate Ester") (0.56 Kg), 97.6% strength, was obtained, single impurity of 1.05% and total impurities of 1.76%.

EXAMPLE 8

Preparation and Purification of [2-(8,9-Dioxo-2,6-diazabicyclo[5.2.0]non-1(7)-en-2-yl)ethyl] phosphonic Acid Bromotrimethylsilane, 97.6% (0.55 Kg, 3.59 moles) was added at room temperature to a stirring suspension of dimethyl phosphonate ester (0.46 Kg, 1.56 moles) in acetonitrile (4.1 L). The resulting solution is then added to stirring acetonitrile-water. The titled phosphonic acid precipitated out of solution as cream-colored solids. The slurry was cooled to 0° C. and the product collected by filtration. The wet cake was stirred in water and 30% NaOH added to a pH of 13. A solution formed. Hydrochloric acid was added to a pH of 1.0. The titled phosphonic acid precipitated out of solution as white-colored solids. The product was collected on a Buchner and washed with ice-cold water. The titled phosphonic acid was then purified by recrystallization from water. The wet cake was dissolved in 12 parts water, filtered through paper on a Buchner, and the filtrate concentrated. Upon cooling The titled phosphonic acid crystallized out of solution. The slurry was cooled to 0° C. and collected on a Buchner. The cake was washed with water, dried in a vacuum oven at 65° C. to afford the titled phosphonic acid, purified in an 86% yield, 99.9% strength, single impurity, 0.05%, total impurities, 0.13%.

We claim:

1. A process for the preparation of [2-((8,9)-dioxo-2,6-diazabicyclo[5.2.0]non-1(7)-en-2-yl)ethyl]phosphonic acid which comprises the following steps:

a) reacting a 3,4-di-$C_1$–$C_4$alkoxycyclobut-3-en-1,2-dione with a di-$C_1$–$C_6$alkyl ester of N-[3-(t-butyloxycarbonylantino)propyl]-2-aminoethylphosphonic acid to give 3-[[2-(di-$C_1$–$C_6$alkoxyphosphoryl)ethyl]-(2-$C_1$–$C_6$alkoxy-3,4-dioxo-1-cyclobuten-1-yl)amino]propyl-carbamic acid tert-butyl ester;

b) deprotecting the 3-amino group of the product of step (a);

c) cyclizing the product of step (b) to form the bicyclic intermediate [2-((8,9)-dioxo-2,6-diazabicyclo[5.2.0] non-1(7)-en-2-yl)ethyl]phosphonic acid di-$C_1$–$C_6$alkyl ester; and d) hydrolyzing the di-$C_1$–$C_6$alkyl ester of step (c) to the phosphonic acid product.

2. A process according to claim 1 wherein the reactions of steps (a), (b) and (c) are carried out in situ.

3. A process according to claim 1 wherein the reaction of step (a) is carried out in anhydrous methanol or ethanol at ambient temperature.

4. A process according to claim 1 wherein the reaction of step (b) is carried out in methylene chloride at –5° C. to 25° C.

5. A process according to claim 1 wherein the reaction of step (d) is carried out in methylene chloride or acetonitrile at about 20° C.

6. A process according to claims 1 wherein the 3,4-di-$C_1$–$C_4$ alkoxycyclobut-3-en-1,2-dione is 3,4-diethoxycyclobut-3-en-1,2-dione.

7. A process according to claims 1 wherein the di-$C_1$–$C_6$alkyl ester of N-[3-(t-butyloxy-carbonylamino)propyl]-2-aminoethylphosphonic acid is prepared by a process which comprises reacting a vinylphosphonate di-$C_1$–$C_6$alkyl ester with 3-aminopropyl carbamic acid 1,1-dimethylethyl ester.

8. A process for the preparation of N-[3-(t-butyloxycarbonylamino)propyl]-2-aminoethylphosphonic acid di-$C_1$–$C_6$alkyl ester which comprises reacting a vinylphosphonate di-$C_1$–$C_6$alkyl ester with 3-aminopropyl carbamic acid 1,1-dimethylethyl ester.

9. A process according to a claim 7 wherein the vinylphosphonate di-$C_1$–$C_6$ alkyl ester is dimethyl vinylphosphonate or diethyl vinylphosphonate.

10. A process according to claim 7 wherein the reaction of the vinylphosphonate di-$C_1$–$C_6$alkyl ester with 3-aminopropyl carbamic acid 1,1-dimethylethyl ester is carried out in anhydrous methanol at about 20° C.

11. A process according to claim 1 wherein the N-[3-(t-butyloxycarbonylamino)propyl]-2-aminoethylphosphonic acid di-$C_1$–$C_6$alkyl ester is N-[3-(t-butyloxycarbonylamino)propyl]-2-aminoethylphosphonic acid dimethyl ester or N-(3-(t-butyloxycarbonylamino)propyl]-2-aminoethylphosphonic acid diethyl ester.

12. A process according to claim 1 wherein step d) is carried out by treating the di-$C_1$–$C_6$ alkyl ester of step c) with bromotrimethylsilane.

13. A process according to claim 8 wherein the vinylphosphonate di-$C_1$–$C_6$ alkyl ester is dimethyl vinylphosphonate or diethyl vinylphosphonate.

14. A process according to claim 8 wherein the reaction of the vinylphosphonate di-$C_1$–$C_6$ alkyl ester with 3-aminopropyl carbamic acid 1,1-dimethylethyl ester is carried out in anhydrous methanol at about 20° C.

15. A process according to claim 9 wherein the reaction of the vinylphosphonate di-$C_1$–$C_6$ alkyl ester with 3-aminopropyl carbamic acid 1,1-dimethylethyl ester is carried out in anhydrous methanol at about 20° C.

* * * * *